(12) United States Patent
Dhere et al.

(10) Patent No.: US 8,795,686 B2
(45) Date of Patent: Aug. 5, 2014

(54) STABLE, DRIED ROTAVIRUS VACCINE, COMPOSITIONS AND PROCESS FOR PREPARATION THEREOF

(75) Inventors: Rajeev M. Dhere, Pune (IN); Sambhaji S. Pisal, Pune (IN); Jagdish K. Zade, Pune (IN)

(73) Assignee: Serum Institute of India, Pune (IN)

( * ) Notice: Subject to any disclaimer, the term of this patent is extended or adjusted under 35 U.S.C. 154(b) by 493 days.

(21) Appl. No.: 13/056,557

(22) PCT Filed: Nov. 6, 2009

(86) PCT No.: PCT/IN2009/000629
§ 371 (c)(1),
(2), (4) Date: Jan. 28, 2011

(87) PCT Pub. No.: WO2010/146598
PCT Pub. Date: Dec. 23, 2010

(65) Prior Publication Data
US 2011/0177119 A1     Jul. 21, 2011

(30) Foreign Application Priority Data
Nov. 7, 2008   (IN) .......................... 2365/MUM/2008

(51) Int. Cl.
*A61K 39/15*         (2006.01)
(52) U.S. Cl.
USPC ..................................... 424/215.1; 435/235.1

(58) Field of Classification Search
None
See application file for complete search history.

(56) References Cited

U.S. PATENT DOCUMENTS

| | | | |
|---|---|---|---|
| 6,403,098 B1 * | 6/2002 | Burke et al. | ............... 424/215.1 |
| 2003/0092145 A1 | 5/2003 | Jira et al. | |
| 2006/0233830 A1 | 10/2006 | Wong et al. | |
| 2007/0031451 A1 | 2/2007 | Slifka et al. | |
| 2008/0096264 A1 | 4/2008 | Murphy et al. | |
| 2008/0274197 A1 | 11/2008 | Mizuno | |

FOREIGN PATENT DOCUMENTS

WO   WO 02/09749   *  2/2002

OTHER PUBLICATIONS

International Search Report for PCT/IN09/00629 dated May 2, 2011.

* cited by examiner

*Primary Examiner* — Mary E Mosher
*Assistant Examiner* — Myron Hill
(74) *Attorney, Agent, or Firm* — Knobbe Martens Olson & Bear LLP

(57) ABSTRACT

The present invention provides novel lyophilized rotavirus vaccine formulations and methods of their preparation. The formulations include vaccine stabilizers, resulting in a vaccine formulation with enhanced stability and minimal loss of potency. The rotavirus vaccine formulations comprise an advantageous ratio of a disaccharide (such as sucrose) to an amino acid (such as glycine). The lyophilization results in a virus formulation with 100% virus preservation and residual moisture from about 0.8% to 1.4%.

7 Claims, 1 Drawing Sheet

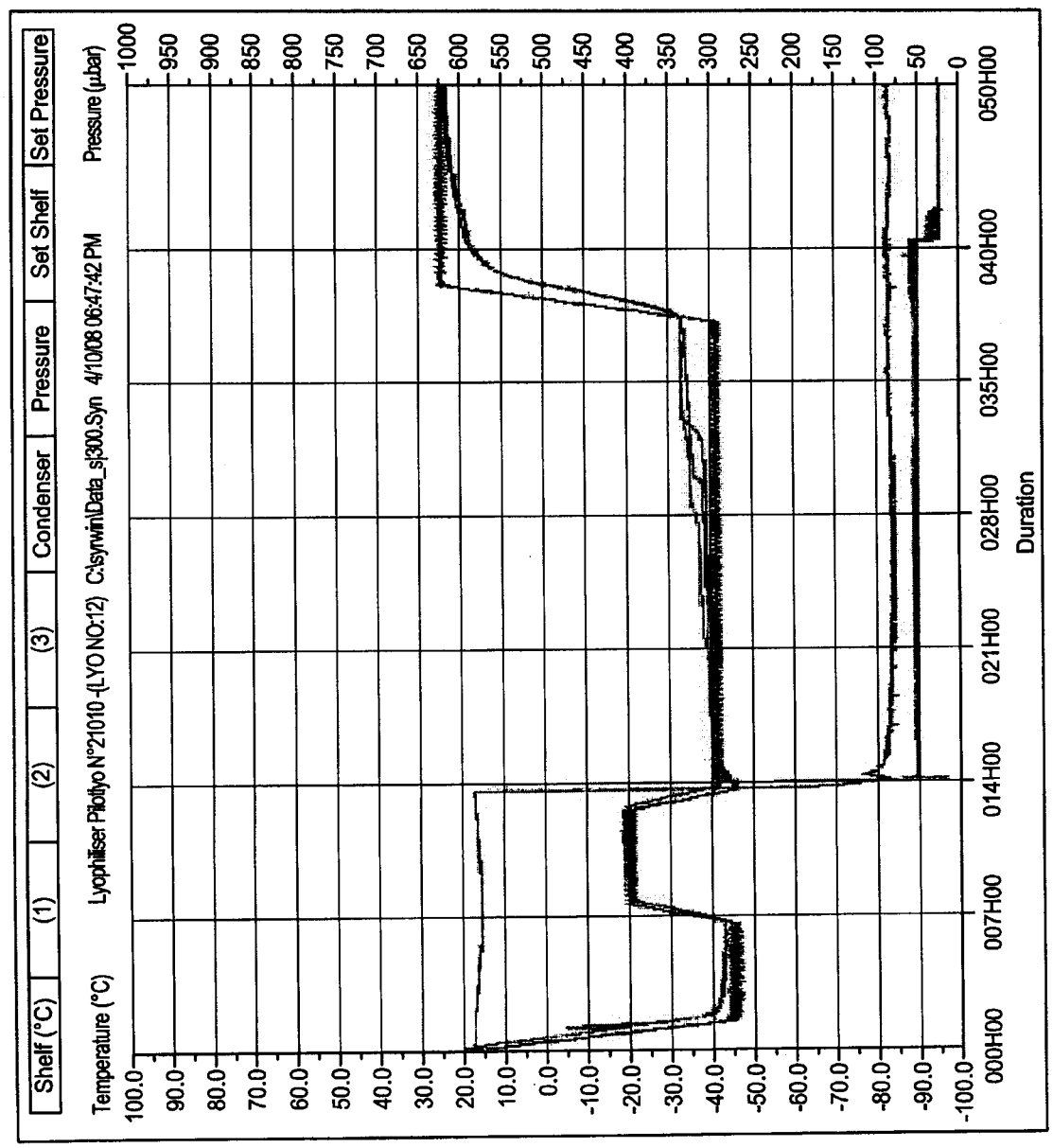

STABLE, DRIED ROTAVIRUS VACCINE, COMPOSITIONS AND PROCESS FOR PREPARATION THEREOF

CROSS REFERENCE TO RELATED APPLICATIONS

This application claims the benefit and priority to and is a U.S. National Phase Application of PCT International Application Number PCT/IN2009/000629, filed on Nov. 6, 2009, designating the United States of America and published in the English language, which is an International Application of and claims the benefit of priority to Indian Patent Application No. 2365/MUM/2008, filed on Nov. 7, 2008. The disclosures of the above-referenced applications are hereby expressly incorporated by reference in their entireties.

FIELD OF INVENTION

The instant invention is related to a Rotavirus Vaccine composition that can be used to prevent infection of one or more strains of Rotavirus, wherein the stabilizers and the drying process provides solid-state formulation with minimal loss of potency.

BACKGROUND OF INVENTION

Rotaviruses are consistently shown to be the single most important cause of severe diarrhea of infants and young children in both developed and developing countries. The consequences of rotavirus diarrhea are staggering as they account for up to 592,000 deaths annually in the under 5-year age group, predominantly in the developing countries (Parashar et al, Emerg. Infect. Dis., 2003, 9:565-572). It has recently been estimated that 1 in 200 children in developing countries will die from rotavirus diarrhea (Glass et al, Lancet, 2004, 363:1547-1550). In the United States, in the under 5-year age group, it was estimated that annually rotaviruses are responsible for 2,730,000 episodes of diarrheal illness, 410,000 visits, to a physician, 160,000 emergency room visits, 50,000 hospitalizations, and 20 deaths (Tucker et al., JAMA, 1998, 279:1371-1376). Thus, the need for a rotavirus vaccine in both developed and developing countries has received national and international endorsement.

WO2007009081 had proposed the use of a hexavalent bovine rotavirus (UK)-based vaccine for developing countries to cover not only the standard serotypes G1 through G4 but also emerging serotypes G8 and G9.

Development of Hexavalent Rotavirus vaccine comprising of standard G1-G4 strains and G9, G8 strains for a broader degree of protection has been previously discussed see Albert Z. Kapikian et. al. "A Hexavalent human Rotavirus-bovine Rotavirus reassortant vaccine designed for use in developing countries"; National Institutes of Health; Journal of infectious diseases; 2005; 192; S22-9 Rotavirus strains may lose viability during drying process and storage. It has been reported previously that lyophilization causes upto 30% loss in virus potency.

Protein formulations containing sucrose-glycine combination have been described by Wei Liu et. al. "Freeze drying of Proteins from a sucrose-glycine excepient system: Effect of formulation composition on initial recovery of protein activity"; AAPS Pharm Scitech; Feb. 11, 2005; 6(2); E150-E157

A lyophilized rotavirus vaccine formulation according to U.S. Pat. No. 6,616,931, U.S. Pat. No. 6,403,098 & U.S. Pat. No. 5,932,223 comprising a strain of rotavirus about $1\times10^5$ to about $1000\times10^5$ pfu/mL, a sugar 1-20% (w/v), Phosphate about 0.05-2 M and a) 0.5%-1.25% of recombinant human serum albumin or b) 0.1%-1.25% of an amino acid (glutamate, glutamine or arginine). Further the patents also discuss improved stability of lyophilized rotavirus formulation by including glycine (1%) in the sucrose/mannitol stabilizer.

There remains a distinct need for rotavirus vaccine formulations with improved viability and stability. None of the prior art stabilizers improve viability & stability. Further for worldwide distribution of rotavirus vaccines, it is necessary to formulate vaccines such that they are stable under a variety of environmental conditions.

Surprisingly, it has now been discovered that a) stabilizer composition comprising of combination of Sucrose and Glycine and b) optimal lyophilization cycle results in a Rotavirus formulation with a moisture content less than 3% and 100% individual virus preservation.

SUMMARY OF INVENTION

The present invention relates to composition containing one or more stabilizers that enable preparation of solid-state, stable Rotavirus vaccine.

The present invention provides novel formulations of rotaviruses useful as vaccines and methods for their preparation.

The present invention relates to vaccine stabilizers, vaccine formulations, preferably lyophilized monovalent & multivalent Rotavirus vaccines which impart increased stability and viability.

The vaccine formulation of the present invention comprises advantageous ratio of a disaccharide (e.g. Sucrose) and an amino acids (e.g glycine) as stabilizer components.

According to the present invention annealing is preferably done at $-20°$ C. The primary drying is carried below Tg, wherein the maximum product temperature during first 1200 min of sublimation does not exceed $-32°$ C.

ADVANTAGES OF THE INSTANT INVENTION

Rapid and uniform Lyophilization is achieved.
Cosmetically carrom pieces like cake with good solubility in antacid diluent having moisture range 0.8 to 1.5% was produced. Residual moisture content less than 3%.
The composition of stabilizer showed excellent preservation efficiency (Range 60-100%) by lyophilization and spray drying.
The lyophilized and spray dried products showed good stability (viability) while processing and at cold storage.
Rapid reconstitution.

BRIEF DESCRIPTION OF THE DRAWINGS

FIG. 1 is a graphical representation depicting a lyophilization result.

DETAILED DESCRIPTION OF THE INVENTION

The invention comprises a lyophilized live rotavirus vaccine formulation that comprises from about 2% w/v to about 20% w/v Sucrose & 2% w/v to about 20% w/v glycine. Within the foregoing range, useful subsets are from about 3% w/v to about 10% w/v of Sucrose & from about 3% w/v to about 10% w/v of Glycine. Surprisingly, such advantageous combination of sucrose and glycine results in increased stability and improved viability of the live rotavirus vaccine.

According to the present invention the advantageous stabilizer composition can be used for monovalent and multivalent formulations wherein the multivalent formulations can be selected from, but not limited to divalent, trivalent, tetravalent and pentavalent.

Rotavirus strains useful in the present invention can be selected from but not limited to Serotype G1, G2, G3, G4, G8, G9, P1, P2 and P3

According to one aspect of the present invention the disaccharide of the vaccine formulation can be selected from a group of, but not limited to sucrose, mannitol, trehalose, maltose and lactose.

Another aspect of the present invention is that the aminoacid of the vaccine formulation can be selected from a group of, but not limited to leucine, iso-leucine, histidine, glycine, glutamine, arginine or alanine.

Additionally the stabilizer composition of the instant invention can comprise or omit additional components such as protein hydrolysate, Human Serum Albumin & partially hydrolyzed gelatin.

The preferred component ranges disclosed in this specification allow for generation of vaccine formulations which, among other characteristics, exhibit improved viability and stability over vaccine formulations known in the art. Stabilizer compositions I-IV as exemplified in this specification will direct the artisan of ordinary skill to generate additional vaccine formulations based on the dual presence of sucrose and glycine within the disclosed ranges. In other words, variations in ratios, concentrations and presence of additional components for each formulation is contemplated.

The ranges of various stabilizer and final vaccine formulations are presented on a w/v basis. One of ordinary skill in the art will be well aware that differing volumes of stabilizer to vaccine may be utilized to practice the claimed invention, which in turn will require changes to the concentration of stabilizer components. The invention is exemplified, but by no means limited to, utilization of 1:1.5 stabilizer:virus combination to generate the final vaccine for lyophilization. However, the artisan may choose different ratios or use bulk viral preparations with altered concentration of major chemical components.

Therefore, the essence of the invention centers around an advantageous combination of sucrose and glycine in the vaccine formulation prior to lyophilization. Especially preferred formulation is prepared by utilizing stabilzer composition I. As disclosed in this section as well as the foregoing examples, a disaccharide (e.g., sucrose) and amino acid (e.g., glycine) can be added in a ratio of about 0.5:1 to about 1:5 to generate a vaccine stabilizer for combination with bulk viral preparations to generate vaccine formulations for lyophilization which result in the before-mentioned stability and viability. Within the foregoing range, useful ratio of sucrose to glycine can be 1:1

The Lyophilization cycle for formulations can comprise a) product loading can be performed at temperatures between 20 to 5° C.; b) Stepwise freezing with hold at each temperature, wherein freezing can be done below −32° C. and preferably −30° C. to −45° C. at a freezing rate of 0.5 to 1° C./min; c) Annealing at −20° C. for 5 hrs can be followed by freezing at −45° C. for 1 hr; d) stepwise rise in temperature during primary drying can comprise of holding at each temperature sufficiently, resulting in sublimation at −32° C. for 20 hrs under pressure of about 55 μbar; e) secondary drying can involve heating product at the rate of 0.5 to PC/min, at 25° C. to 30° C. for 6-10 hrs under pressure of 55 μbar. The total duration of the lyophilization cycle can be 48 hrs. Variations in temperature and cycle duration as per vial specification and lyophilizer design are contemplated.

One or more strains of Rotavirus, against which protection is required, can be cultured in appropriate medium and allowed to grow to the desired level. The pooled virus broth can be mixed with the stabilizer composition in appropriate ratio and then can be subjected to drying process. The drying can be effected by freeze dryer or spray dryer.

Example 1

Sample Collection and Virus Isolate

Ten stool specimens from the diarrhoeal infants were obtained from a private clinic. The stool was collected in sterile container and was stored at 4° C. for 6-10 hrs after collection or at −20° C. for long duration. Three stool specimens were positive for group A rotavirus tested by ELISA using rotavirus antigen detection kit from Generic Assay, Germany. All three specimens were tried to isolate on MA104 (Monkey kidney) cells. One out of three shown a clear cytopathic effect on MA104 cell monolayer, which was harvested after freezing at −70° C. and thawing at 37° C. The harvested virus was stored at −70° C. in 10 ml aliquots. The same virus was used for further infection of MA104 cell as and when required. The isolate was named as SIIL-ROTA-02. The SUL-ROTA-02 isolate was characterized by RT-PCR using the serotype specific primers and was designated as G1 serotype.

Example 2

106.3 gm of MEM powder was dissolved in 9 lit water for injection. 3 gm of Glutamine and 15 gm of Sodium Bicarbonate was dissolved in MEM solution.

The rotavirus strain SIIL-ROTA-02(G1) was cultured using MEM (MEM composition, refer Table 1). The individual virus pool containing MEM were used for preparing final bulk (refer Table 2 for Virus composition in final Bulk). Four different stabilizer mixtures with additive concentrations outlined below were studied. The pH of medium was adjusted to 6.0-8.5 more specifically 7.4 with about 10 ml of 0.1N HCl. The stabilizer solutions were autoclaved or membrane filtered at 2-10× concentration. The virus as 60 parts was combined with 40 parts of each stabilizer composition.

For freeze drying, one ml of final bulk was filled in glass vials (4 ml) (USP Type 1) and 200 vials of each bulk were set in for lyophilization.

TABLE 1

MEM COMPOSITION

| Components | Conc. |
|---|---|
| CALCIUM CHLORIDE (ANHYDR.) | 140 mg/l |
| MAGNESIUM SULPHATE (ANHYDR.) | 98 mg/l |
| POTASSIUM CHLORIDE | 400 mg/l |
| POTASSIUM PHOSPHATE MONOBASIC (ANHYDR.) | 60 mg/l |
| SODIUM CHLORIDE | 8000 mg/l |
| SODIUM PHOSPHATE DIBASIC (ANHYDR.) | 48 mg/l |
| L-ARGININE HCl | 126 mg/l |
| L-CYSTINE.2HCl | 31 mg/l |
| L-GLUTAMINE | 292 mg/l |
| L-HISTIDINE.HCl•H20 | 42 mg/l |
| L-ISOLEUCINE | 52 mg/l |
| L-LEUCINE | 52 mg/l |
| L-LYSINE.HCl | 73 mg/l |
| L-METHIONINE | 15 mg/l |

TABLE 1-continued

MEM COMPOSITION

| Components | Conc. |
|---|---|
| L-PHENYLALANINE | 32 mg/l |
| L-THREONINE | 48 mg/l |
| L-TRYPTOPHAN | 10 mg/l |
| L-TYROSINE.2NA•2H2O | 52 mg/l |
| L-VALINE | 46 mg/l |
| CHOLINE CHLORIDE | 1 mg/l |
| FOLIC ACID | 1 mg/l |
| I-INOSITOL | 2 mg/l |
| NIACINAMIDE | 1 mg/l |
| D-PANTHOTHENIC ACID (HEMICALCIUM) | 1 mg/l |
| PYRIDOXAL.HCl | 1 mg/l |
| RIBOFLAVIN | 0.1 mg/l |
| THIAMINE.HCl | 1 mg/l |
| GLUCOSE | 1000 mg/l |
| PHENOL RED.NA | 10 mg/l |
| NaHCO3 (Additional) | 0.75 gm/l |
| Glutamine (Additional) | 350 mg/l |
| HCL (1N) | 1.25 ml/l |

TABLE 2

Virus Composition Of Final Bulk

| Serotype | Number Of Particles | Corresponding Titre |
|---|---|---|
| Serotype G1 | 8713560 | 6.9 |

Example 3 a) Stabilizer Mixture I 25 gm of sucrose was dissolved in 100 ml water for injection. Similarly, 25 gm of glycine was dissolved in 100 ml water for injection. The solubility of glycine is aided by presence of salt, 0.88% NaCl. These are 5× solutions. The mixed solution produces 2.5× of each component. 2.5× stabilizer solution was filtered using 0.2 μm membrane.

The pooled virus as 60 parts was combined with 40 parts of each stabilizer composition.

b) Optimized Lyophilization Cycle

"Lyophilization Cycle employed for Monovalent Formulation, can also be used for Multivalent formulations"

TABLE 3

Lyophilization Cycle

| PRECOOLING | | | |
|---|---|---|---|
| Shelf pre-cooling: | No | | |
| FREEZING | | | |
| Shelf T control | Final T (° C.) | Ramp duration (min) | Soak duration (min) |
| Ramp 1 & Soak 1 | −45 | 90 | 300 |
| Ramp 2 & Soak 2 | −20 | 60 | 300 |
| Ramp 3 & Soak 3 | −45 | 60 | 1 |
| Transition (Freezing ----> Condenser cooling) | Product temperature + Duration | −40° C. + 811 min | |
| Hold product under low T (min): | 1 | | |
| CONDENSER COOLING | | | |

TABLE 3-continued

Lyophilization Cycle

| Condenser T before chamber evac. (° C.): | −50 | | |
|---|---|---|---|
| Alarm: Cond T: | −40 | | |
| CHAMBER EVACUATION | | | |
| Alarm: P1 set-point: | 150 | | |
| Alarm: P2 set-point: | 100 | | |
| Continue evacuation under P2 (min): | 1 | | |
| Alarm: Chamber evac. too long (min): | 90 | | |
| SUBLIMATION | | | |
| Shelf T control | Final T (° C.) | Ramp duration (min) | Soak duration (min) |
| Ramp 1 & Soak 1 | −41 | 1 | 1440 |
| Ramp 2 & Soak 2 | 25 | 120 | 1 |
| Chamber pressure control | Chamber pressure (μbar) | | Soak duration (min) |
| Soak 1 | 55 | | 1561 |
| Max. product temp, during sublim. (° C.) | −35 | | |
| Duration from begin, of sublim. (min) | 1440 | | |
| Alarm: Shelf Temperature (° C.) | 5 | | |
| Transition End of Sublimation | Product temperature + Duration | 18° C. + 1562 min | |
| SECONDARY DRYING | | | |
| Shelf T control | Final T (° C.) | Ramp duration (min) | Soak duration (min) |
| Ramp 1 & Soak 1 | 25 | 1 | 480 |
| Chamber pressure control | Chamber pressure (μbar) | | Soak duration (min) |
| Soak 1 | 25 | | 481 |
| Transition end of Sec. drying | Keyboard | | |
| Transition Triggered | Manual | | |
| STOPPERING POST COOLING | | | |
| Pressurisation | No | | |
| Stoppering | No | | | c) Result: Lyophilization

FIG. 1 Indicates a Lyophilization Result.

The results indicate that uniform cylindrical cakes were obtained at the bottom of vials. The final cake was soluble in sodium citrate buffer as well as in water for injection. There was no migration or deposition of soluble micronutrients indicating uniform sublimation. Also the residual moisture was 0.8% to 1.4% i.e. below 3% and reconstitution time was less than 30 sec. 100% virus preservation was observed.

TABLE 4

Virus titres for Rotavirus Lyophilized Vaccine

| Virus Serotype | Set Titers Before Lyophilization (Particle number) | Titers After Lyophilization (Particle number) | Preservation Efficiency |
|---|---|---|---|
| Rota-G1 | 7.14 ($1.40 \times 10^7$) | 7.18 ($1.53 \times 10^7$) | 101% | d) Stability Testing

TABLE 5

Shelf life of the Monovalent Rotavirus Vaccine at 25° C. for 6 months

| Freq. Month | Description Criterion: Yellowish White Mass | Virus Content Should not be less than 5.000 $Log_{10}$ $CCID_{50}$/ml | Potency | pH |
|---|---|---|---|---|
| 0 | Pass | 7.281 | 7.281 | 7.45 |
| 1 | Pass | 6.680 | 7.125 | 7.48 |
| 2 | Pass | 6.812 | 7.250 | 7.4 |
| 3 | Pass | 6.968 | 7.2 | 7.38 |
| 4 | Pass | 7.093 | 7.125 | 7.46 |
| 5 | Pass | 7.25 | 7.25 | 7.5 |
| 6 | Pass | 7.3 | 7.2 | 7.44 |

No significant loss found; indicating that the Monovalent Multivalent vaccine is stable upto 6 month at 25° C.

TABLE 6

Shelf life of Monovalent Rotavirus Vaccine at 37° C. for 15 months

Original titre Incubation  7.14 $CCID_{50}$/ml

| Duration | Vial-1 | Vial-2 |
|---|---|---|
| 1 month | 6.825 | 6.750 |
| 2 month | 6.5 | 7.125 |
| 3 month | 6.875 | 7.250 |
| 4 month | 7.0 | 7.125 |
| 5 month | 7.0 | 6.825 |
| 6 month | 7.3 | 7.125 |
| 9 month | 7.0 | 6.750 |
| 12 month | 6.750 | 6.7 |
| 15 month | 6.825 | 6.750 |

No significant loss found; indicating that the Monovalent Rotavirus vaccine is stable upto 15 month at 37° C.

Rotavirus serotyping is based on a single VP7 protein which has less or no role in determining the stability of the virus, hence formulation used for a monovalent vaccine can also be used for a multivalent composition. Further solubility of the cake in citrate buffer as well as in water for injection is not affected by presence of single or multiple strains. Thus, the formulation demonstrated above can be used for any monovalent as well as for multivalent rotavirus vaccine.

Example 4

Stabilizer Mixture II and its Lyophilization Cycle Specifications

Disaccharide 2-25% w/v (one or more selected from Mannitol, Sucrose, Trehalose) Protein Hydrolysate (LAH) 1-20% w/v, Alternately, amino acids (one or more selected from leucine, iso-leucine, histidine, glycine or alanine) were used as replacement for protein hydrolysate in concentrations of 5-100 mM. The vials were rapidly cooled to −40 to −50° C., held for 2-8 hrs. The mixture was annealed sufficiently at −20 to −30° C., whenever crystallization was desired. The vials were primary dried below eutectic temperatures for 7 to 30 hrs at a pressure of less than 300 μbar. The evaporative drying was performed at 25° C. for 2-12 hrs, at pressure less than 300 μbar.

The results indicate that non-uniform cakes were obtained. Considerable Potency losses were observed across lyophilization and filling for the above formulation.

The acceptance criteria for % residual moisture was NMT 3%. However for this formulation % mositure was 4%, hence acceptance criteria was not met. Thus this formulation was not studied further.

Example 5

Stabilizer Mixture III and its Lyophilization Cycle Specifications

| Human serum albumin | 1-20% w/v |
|---|---|
| Mannitol | 1-20%, w/v |

Equivalent mixture of two disaccharides (mannitol and sucrose) can be used as alternative to mannitol alone.

The vials were rapidly cooled to −30° C. and held for 6 hrs. The freezing was further continued to −55° C. and held for 5 hrs. The vials were primary dried below eutectic temperatures for 7-25 hrs at a pressure, of less than 300 μbar. The evaporative drying was performed at 32° C. for 4-8 hr, at pressure less than 175 μbar.

The results indicate that non-uniform cakes were obtained. Considerable Potency losses were observed across lyophilization and filling for the above formulation. The acceptance criteria for % residual moisture was NMT 3%. However for this formulation % residual mositure was 4%, hence acceptance criteria was not met. Thus this formulation was not studied further.

Example 6

Stabilizer Mixture IV and its Lyophilization Cycle Specifications

| Partially hydrolyzed gelatin | 3-15% w/v |
|---|---|
| Sorbitol | 5-20% w/v |

The vials were frozen at freezing rate of 0.2° C./min to reach −45° C. and held for at least 10 hr. The vials were primary dried below eutectic temperatures for 30 hrs at a pressure of less than 200 μbar. The evaporative drying was performed at 37° C. for 4-10 hr, at pressure less than 100 μbar.

The results indicate that non-uniform cakes were obtained. Considerable Potency losses were observed across lyophilization and filling for the above formulation. The acceptance criteria for % residual moisture was NMT 3%. However for this formulation % residual moisture was 5%, hence acceptance criteria was not met. Thus this formulation was not studied further.

Although lyophilization is preferred mode of drying the above mentioned rotavirus compositions, spray drying and for vacuum drying might produce desired results.

REFERENCES

1. Kapikian et. al., A hexavalent human rotavirus-bovine rotavirus reassortant vaccine designed for use in developing countries and delivered in a schedule with the potential to eliminate the risk of intussusception.

The Journal of Infectious Diseases, 2005; 192(suppl1): S22-S29.
2. Glass et. al., The future of rotavirus vaccines: a major setback leads to new opportunities. Lancet, 2004; 363: 1547-50.

3. Liu et. al., Freeze drying of proteins from a sucrose-glycine excipient system: Effect of formulation composition on initial recovery of protein activity. AAPS PharmaSci Tech, 2005; 6(2): E150-E157.

4. Wang W. Lyophilization and development of solid protein pharmaceuticals. Int J Pharma, 2000; 203:1-60.
5. Pyne et. al., Phase transitions of glycine in frozen aqueous solutions and during freeze drying. Pharm Res, 2001 October; 18(10): 1448-54.
6. Akers et. al., Glycine crystallization during freezing: The effects of salt form, pH, and ionic strength. Pharm Res, 1995; 12(10): 1457-1461(5).
7. Pisal et. al., Vacuum drying for preservation of lasota virus: Effect of protectants and stability study; AAPS Pharm Sci Tech, 2006; 7(3): Article 60

8. Pikal et. al., Heat and mass transfer scale-up issues during freeze drying: II. Control and characterization of the degree of supercooling. AAPS Pharm Sci Tech, 2004; 5(4): Article 58.

9. Pyne et. al., Solute crystallization in mannitol-glycine systems-implications on protein stabilization in freeze dried formulations. J Pharm Sci, 2003 November; 92(11): 2272-83.

We claim:

1. A lyophilized rotavirus vaccine formulation comprising prior to lyophilization:

a) at least one strain of rotavirus at a concentration from $1\times10^5$ pfu/mL to $1000\times10^5$ pfu/mL;

b) sucrose at a concentration of 5% (w/v); and c) glycine at a concentration of 5% (w/v).

2. The composition of claim 1, further comprising a biologically effective concentration of a cell culture medium.

3. The composition of claim 2, wherein said cell culture medium is Minimum Essential Medium (MEM).

4. A method of preparing a stabilized rotavirus vaccine formulation according to claim 1, comprising:

a) Cultivating at least one strain of rotavirus in MEM additionally containing Glutamine and Sodium Bicarbonate;

b) Preparing a stabilizer comprising, sucrose and glycine;

c) Combining said at least one strain of rotavirus at a concentration from $1\times10^5$ pfu/mL to $1000\times10^5$ pfu/mL prior to lyophilization and said stabilizer so as to obtain a mixture of said rotavirus and stabilizer wherein the mixture has sucrose at a concentration of 5% (w/v) and glycine at a concentration of 5% (w/v); and d) Lyophilizing the mixture of stabilizer and rotavirus for 30 hrs to 60 hrs, thereby producing a lyophilized form of vaccine with a residual moisture content from 0.8% to 1.4%.

5. The method of claim 4, wherein the lyophilization is performed by:

a) Loading a lyophilizer with the mixture of said rotavirus and stabilizer at temperatures between 25 to −50° C.;

b) Stepwise freezing said mixture of rotavirus and stabilizer with a hold at each temperature, wherein freezing is done below −32° C. at a freezing rate ranging from 0.5 to 5° C./min.;

c) Annealing said mixture of rotavirus and stabilizer at a temperature ranging from −15° C. to −25° C. for 5 hrs followed by freezing at −45° C. for 1 hr;

d) Stepwise raising of the temperature during primary drying for 10 to 30 hrs under a pressure of 55 μbar so as to achieve a sublimation at −32° C.; and e) providing a secondary drying, wherein said mixture of rotavirus and stabilizer is heated at the rate of 0.5 to 1° C./min, at 25° C. to 30° C. for 6-10 hrs under a pressure of 55 μbar.

6. The method of claim 5, wherein the lyophilization is performed by:

a) Loading a lyophilizer with the mixture of said rotavirus and stabilizer at temperatures between 20 to 5° C.;

b) Stepwise freezing said mixture of rotavirus and stabilizer with a hold at each temperature, wherein freezing is done below −32° C. at a freezing rate ranging from 0.5 to 1° C./min.;

c) Annealing said mixture of rotavirus and stabilizer at a temperature of −20° C. for 5 hrs followed by freezing at −45° C. for 1 hr;

d) Stepwise raising of the temperature during primary drying for at least 20 hours under a pressure of 55 μbar so as to achieve a sublimation at −32° C.; and e) providing a secondary drying, wherein said mixture of rotavirus and stabilizer is heated at the rate of 0.5 to 1° C./min, at 25° C. for 8 hrs under a pressure of 55 μbar.

7. The method of claim 5, wherein the lyophilization cycle duration ranges from 30 to 60 hrs.

* * * * *